(12) United States Patent
Richart et al.

(10) Patent No.: US 10,327,857 B2
(45) Date of Patent: Jun. 25, 2019

(54) MEDICAL ASSEMBLY COMPRISING A MEDICAL ARTICLE AND A PACKAGE CONTAINING SAID ARTICLE

(75) Inventors: Olivier Richart, Lagord (FR); Gregoire Larche, Cholet (FR); Jean-Pierre Podgorski, Saint Crespin sur Moine (FR)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 229 days.

(21) Appl. No.: 14/112,355

(22) PCT Filed: Apr. 19, 2012

(86) PCT No.: PCT/FR2012/050852
§ 371 (c)(1),
(2), (4) Date: Oct. 31, 2013

(87) PCT Pub. No.: WO2012/172215
PCT Pub. Date: Dec. 20, 2012

(65) Prior Publication Data
US 2014/0042050 A1    Feb. 13, 2014

Related U.S. Application Data

(63) Continuation-in-part of application No. 13/583,801, filed as application No. PCT/FR2011/050943 on Apr. 22, 2011, now Pat. No. 9,265,579.

(30) Foreign Application Priority Data

Apr. 27, 2010  (FR) ...................................... 10 53191
Apr. 22, 2011  (FR) ...................................... 11 53520

(51) Int. Cl.
*A61B 50/00*    (2016.01)
*A61B 50/30*    (2016.01)
(Continued)

(52) U.S. Cl.
CPC ............ *A61B 50/30* (2016.02); *A61B 17/865* (2013.01); *A61F 2/0095* (2013.01);
(Continued)

(58) Field of Classification Search
CPC . A61C 8/0087; A61F 2/0095; B65D 77/0486; A61B 17/865
(Continued)

(56) References Cited

U.S. PATENT DOCUMENTS 4,712,681 A * 12/1987 Branemark et al. .......... 206/438
4,856,648 A    8/1989 Krueger
(Continued)

FOREIGN PATENT DOCUMENTS

DE       10146905       7/2003
EP       1523955 A1     4/2005
(Continued)

OTHER PUBLICATIONS

International Search Report, dated Mar. 4, 2013, from corresponding PCT application.
(Continued)

*Primary Examiner* — Ernesto A Grano
(74) *Attorney, Agent, or Firm* — Kramer Amado, P.C.

(57) ABSTRACT

A medical assembly, preferably a sterilized one, includes a medical article (5) and a package containing the article, the package including a hollow support element (2) inside which the article (5) is free, a first protective element (3), called a stopper, which can be coupled to the support element (2) of the article, such that the support element (2) has a grip part (20) that protrudes from the stopper (3), and a second hollow protective element (4), called a cover. The cover can be coupled to the stopper (3) in such a way as to delimit, in cooperation with the stopper (3), a chamber (8) inside which there extends the grip part (20) of the support
(Continued)

element, and, in the state when the cover is coupled to the stopper, a part of the stopper (3) protrudes from the cover (4).

20 Claims, 4 Drawing Sheets

(51) Int. Cl.
    *A61B 17/86*     (2006.01)
    *A61F 2/00*     (2006.01)
    *B65D 77/04*     (2006.01)

(52) U.S. Cl.
    CPC .. *B65D 77/0493* (2013.01); *A61B 2050/0054* (2016.02); *A61B 2050/0064* (2016.02); *A61B 2050/0066* (2016.02); *A61B 2050/3006* (2016.02)

(58) Field of Classification Search
    USPC ........................................................ 206/438
    See application file for complete search history.

(56) References Cited

U.S. PATENT DOCUMENTS

| | | | |
|---|---|---|---|
| 5,062,800 A | 11/1991 | Niznick | |
| 5,437,550 A | 8/1995 | Beaty et al. | |
| 5,538,428 A | 7/1996 | Staubli | |
| 5,600,608 A | 2/1997 | Weiss et al. | |
| 5,622,500 A * | 4/1997 | Niznick | 433/173 |
| 5,692,904 A | 12/1997 | Beaty et al. | |
| 5,755,575 A * | 5/1998 | Biggs | 433/173 |
| 6,108,274 A | 8/2000 | Pearce | |
| 6,203,323 B1 | 3/2001 | Beaty et al. | |
| 6,217,332 B1 * | 4/2001 | Kumar | 433/173 |
| 6,247,932 B1 | 6/2001 | Sutter | |
| 6,280,192 B1 * | 8/2001 | Groll et al. | 433/173 |
| 6,483,775 B1 | 11/2002 | Spackman et al. | |
| 6,561,805 B2 * | 5/2003 | Kumar | 433/174 |
| 6,853,604 B2 | 2/2005 | Spackman et al. | |
| 7,120,087 B2 | 10/2006 | Lee et al. | |
| 7,451,870 B2 * | 11/2008 | Donahoe et al. | 206/63.5 |
| 7,854,316 B2 | 12/2010 | Park et al. | |
| 7,921,991 B2 | 4/2011 | Sato et al. | |
| 8,083,054 B2 | 12/2011 | Nihei et al. | |
| 8,181,773 B2 * | 5/2012 | Guenter et al. | 206/63.5 |
| 8,413,811 B1 * | 4/2013 | Arendt | 206/368 |
| 2003/0221977 A1 * | 12/2003 | Kumar et al. | 206/63.5 |
| 2004/0043358 A1 * | 3/2004 | Howlett et al. | 433/141 |
| 2005/0023166 A1 * | 2/2005 | Howlett et al. | 206/369 |
| 2005/0098460 A1 | 5/2005 | Smith et al. | |
| 2009/0065387 A1 | 3/2009 | Bammerlin et al. | |
| 2012/0318697 A1 * | 12/2012 | Stern | 206/514 |

FOREIGN PATENT DOCUMENTS

| | | |
|---|---|---|
| FR | 2581867 A1 | 11/1986 |
| WO | 0002496 | 1/2000 |

OTHER PUBLICATIONS

International Search Report dated Oct. 19, 2011.
Search Report dated Jul. 13, 2015.

\* cited by examiner

Fig. 8

MEDICAL ASSEMBLY COMPRISING A MEDICAL ARTICLE AND A PACKAGE CONTAINING SAID ARTICLE

CROSS-REFERENCE TO RELATED APPLICATIONS

This application is a National Stage of International Application No. PCT/FR2012/050852, filed Apr. 19, 2012, claiming priority to French Patent Application No. 1153520 filed on Apr. 22, 2011. This application is a continuation-in-part of application Ser. No. 13/583,801 (now U.S. Pat. No. 9,265,579), which was filed as the 371 National Stage Entry of PCT/FR2011/050943 on Apr. 22, 2011, claiming priority to FR 1053191 which was filed on Apr. 27, 2010.

BACKGROUND OF THE INVENTION

Field of the Invention

The present invention relates generally to packages for articles, in particular for medical components, preferably sterilized medical components.

The invention relates more particularly to a medical assembly, preferably a sterilized one, comprising a medical article and a package containing said article.

DESCRIPTION OF THE RELATED ART

In the prior art, packages are known that are in the form of external and internal double envelopes of the sachet type, or in the form of double plastic blister shells, or a combination of both, in which an article is contained. In the case of medical components that have to be unpacked in near-aseptic conditions, such packages may pose problems of contamination when the package is passed from one person to another and when said package is being opened. Specifically, from its departure from a work area referred to as dirty, that is to say without any special aseptic conditions, to its arrival in a work area referred to as clean, that is to say a work area in which given aseptic conditions are maintained, for example the "sterile" area of an operating theater, the package arriving in the clean area is contaminated on its outer envelope, which poses a risk of the medical component being contaminated when it is removed from said package.

In order to limit the risk of contamination of the article contained in the package, it is known to open said package in such a way as to cause the article to fall onto a work surface, so as not to have to touch said article. Only the surgeon or a sterile assistant picks up the article. However, the article runs the risk not only of being damaged on impact with the work surface, in the case of a solid article, or even of rolling onto the floor, but also of being contaminated by foreign bodies present on the work surface. It also happens that the operator passes the external envelope of the package to the sterile assistant, who then has to try to take hold of the internal envelope without incurring asepsis. However, there is a very great risk of the assistant touching a contaminated area of the package during this operation, and of the article taken hold of in turn being contaminated.

Document U.S. Pat. No. 5,062,800 describes a medical package for a dental implant, which medical package comprises a support element provided with means for fixing the implant, and a stopper that can be coupled to the support element in such a way that the support element protrudes from said stopper. Said package also comprises a cover that covers the stopper. However, the cover completely covers the length of the stopper, such that the operator has no option other than to empty the content of the cover by causing said content to fall onto a work surface. As has been mentioned above, allowing the implant to fall, if appropriate together with its envelope, may damage said implant and increases the risk of contamination.

In addition, in document U.S. Pat. No. 5,062,800, the implant is fixed to the corresponding support element of the package. This means that the operator has to perform a specific maneuver in order to remove the implant from the support element once the other elements have been withdrawn, which complicates the intervention by the operator and does not allow him to quickly take hold of the implant that he requires. In particular, in the field of emergency surgery or traumatology, the operator who requires said implant must be able to access it as quickly as possible, while of course limiting the risk of contamination of said implant.

The object of the present invention is to make available a package for the packing and unpacking of an article, which package makes it possible to limit the risks of contamination of the article while at the same time permitting easy and quick access to said article.

SUMMARY OF THE INVENTION

To this end, the invention relates to a medical assembly, preferably a sterilized one, comprising a medical article and a package containing said article, said package comprising a hollow support element inside which said article is free, characterized in that said package comprises:

a first protective element, called a stopper, which can be coupled to the support element of said article, preferably by engagement with partial overlap, in such a way that the support element has a grip part that protrudes from said stopper, said support element delimiting on its own, or in cooperation with the stopper, a first chamber that encloses said article, a second hollow protective element, called a cover, said cover being able to be coupled to the stopper, preferably by engagement with partial overlap, in such a way as to delimit, in cooperation with said stopper, a second chamber inside which there extends the grip part of the support element, and in that, in the state when the cover is coupled to the stopper, a part of the stopper protrudes from the cover.

By virtue of the grip part of each protective element and of the support element, which protrudes from the protective element to which it is coupled, the chambers defined by engagement of said elements, with partial overlap, can be opened in order to access the article without ever letting go of or touching said article and with a reduced risk of contamination of the article.

Indeed, when the package is passed from a first person, whose hands are presumed to be "contaminated", to a second person, whose hands are presumed to be "clean", the protective cover can be withdrawn by the first person in such a way as to open the "second" chamber in order to uncover the grip end of the support element of the article and retain, for the second person, only the sub-assembly composed of the stopper and of the support element.

The first person holds said sub-assembly via the end of the stopper remote from the support element and can offer the second person, for example the surgeon, the clean end of the support element, uncovered by the opening of the first chamber.

The stopper and the support element can then be separated in such a way as to open the chamber containing the article. The second person, who thus retains only the support element containing the article, can thus hold the grip end of the support element in his clean hand while taking hold of the article, for example, via his other clean hand.

Such a design of the package according to the invention makes it possible to produce a package with a smaller number of component parts, basically three, in such a way that, when the package is passed from a dirty area to a clean area by way of different persons, neither the support element nor the article are touched by anyone in the dirty area, and the article contained in the support element is never let go of. The risk of contamination is thus very considerably reduced.

In addition, the fact that the article is free inside the support element allows easy and quick access to the article. In particular, in the field of emergency surgery, the person who requires said article must be able to quickly access said article while at the same time limiting the risk of contamination of said article, as is explained in detail below.

According to an advantageous feature of the invention, said stopper comprises a peripheral wall called an internal wall, and a peripheral wall called an external wall which surrounds said internal peripheral wall with clearance in order to define, between said peripheral walls, an annular space for engagement of that part of the cover intended to be coupled to said stopper, the internal peripheral wall defining a space for engagement of that part of the support element intended to be coupled to said stopper.

According to an advantageous feature of the invention, the internal face of the internal peripheral wall of the stopper is provided with retaining means for retaining that part of the support element engaged inside the space delimited by said internal peripheral wall of the stopper.

According to an advantageous feature of the invention, said retaining means comprise lugs which are intended to be in bearing contact with the support element in the state when said support element is engaged in the stopper, and the lugs are distributed on the internal peripheral face of the stopper, about the axis of said stopper, by being spaced apart at angles from one another.

According to an advantageous feature of the invention, each lug comprises a ramp-forming part, directed toward the axis of the stopper starting from a bottom point of the ramp situated at the open end of the stopper to a top point of said ramp situated at the closed end of said stopper, in such a way that, when the support element is engaged inside the space defined by the internal peripheral wall of the stopper, said support element, by bearing on said ramp, pushes said lug radially and deforms the corresponding internal peripheral wall toward the external peripheral wall.

According to an advantageous feature of the invention, the lugs form spacers for maintaining a radial distance between the support element and the internal peripheral wall of the stopper, the spacing between the lugs defining a space for fluid communication between the inside of the peripheral wall of the stopper and the inside of the cover.

According to an advantageous feature of the invention, said external and/or internal peripheral walls of the stopper comprise screwing means for cooperating with complementary screwing means formed on the cover.

According to an advantageous feature of the invention, the internal face of the external peripheral wall of the stopper has a tapping that is able to cooperate with a thread formed on the external face of the peripheral wall of the cover.

According to an advantageous feature of the invention, when said support element delimits on its own said first chamber enclosing said article, said support element is formed by at least two components that can be coupled to/uncoupled from each other, preferably by engagement with partial overlap, in order to form said first chamber enclosing said article.

Thus, the design of the package in the form of a support element coupled to a stopper which delimits, in cooperation with a cover, a chamber in which part of the support element protrudes from the stopper, allows the support element to be passed from a first person to a second person without the first person touching the support element and with a reduced risk of contamination between the first person and the second person, such that the support element enclosing said article arrives at the clean area with a reduced risk of contamination. In addition, the design of the support element in the form of two component parts, which can be coupled in order to delimit a closed cavity (first chamber), makes it possible to protect said article pending its use.

According to an advantageous feature of the invention, when said support element delimits, in cooperation with the stopper, said first chamber enclosing said article, said support element delimits an open cavity intended to be closed by said stopper.

According to such an embodiment, said package can be composed of only three component parts, namely the cover, the stopper, and the support element. Each component part is in the form of a hollow body that is open in the manner of a test tube. Thus, the support element can be coupled to the stopper in order to delimit the first chamber which encloses said article, and the stopper can be coupled to the cover in order to delimit the second chamber which encloses that part of the support element protruding from the stopper.

According to an advantageous feature of the invention, the stopper and the cover are each formed by an elongate hollow body that is open at one end and closed at the other end.

The elongate character of the one or more elements which protect the article, and which are formed by the cover and the stopper, provides the benefit of a safety distance when the chambers are opened while passing the various parts of the package from one person to another.

According to an advantageous feature of the invention, said stopper, and if appropriate the cover, has (have) predefined locations permitting the positioning of at least two fingers, preferably three fingers, of a person in order to allow him to grip said stopper, and if appropriate said cover, in the area of said predefined locations.

Advantageously, said stopper, and if appropriate said cover, has (have) predefined locations permitting the positioning of at least three fingers in order to grip between them said stopper, and if appropriate said cover.

A predefined location of this kind makes it possible to limit the risk of contamination of the support element and therefore of the article contained in said support element.

According to an advantageous feature of the invention, when said cover can be coupled to the stopper by engagement with partial overlap, said stopper has at least one deformable part, preferably at least one deformable wing, which is configured such that, on the one hand, when said deformable part of the stopper is covered by the cover, said part comes to bear against the internal face of the cover in order to allow the stopper to be coupled to the cover by friction, and, on the other hand, such that said part is able to deform in order to permit the separation of the cover from the stopper.

Such a deformable part of the stopper ensures good leaktightness between the stopper and the cover in the coupled state of these two component parts.

According to an advantageous feature of the invention, said support element and protective elements of the package engage each other, with partial overlap, by friction and/or by screwing.

According to an advantageous feature of the invention, the support element and/or the stopper and/or the cover have a part, preferably formed by a membrane, that is impermeable to bacteria but permeable to gases in order to permit gas sterilization of said first chamber and/or of said second chamber.

The invention also relates to a method of unpacking a medical article contained in a package of a medical assembly, preferably a sterilized one, as has been described above, characterized in that said method comprises the following steps:

a) separation of the cover from the stopper by a first person, referred to as the contaminated person, in order to uncover the support element,
b) gripping of the support element by a second person, referred to as the non-contaminated person,
c) separation of said support element from the stopper held by said contaminated person.

According to an advantageous feature of the invention, said method comprises the following additional steps:
d) optionally keeping said support element, which encloses the article, in a stand-by area pending the use of said article,
e) opening the first chamber defined by said support element in order to remove said article therefrom.

These method steps apply in particular to an embodiment of the package according to the invention in which the support element on its own forms said first chamber, and in which said support element is composed of at least two component parts which can be coupled to/uncoupled from each other and which, in the coupled state, delimit a closed cavity forming said first chamber. The first person offers the second person the remaining package composed of the stopper and of the support element, by presenting to him the end of said remaining package formed by said support element. The second person then pulls said support element in such a way as to separate it from said stopper. The support element, which forms a cavity enclosing the article, can then be placed on a table in a decontaminated area pending its use. The embodiment of the support element in the form of a cavity enclosing the article makes it possible to protect said article, which remains inside the support element pending its use, against external contamination. It then suffices for the second person, or another "clean" person, to open the first chamber formed by said support element, by separating at least the two component parts that form said support element.

According to an advantageous feature of the invention, said method comprises, between steps a) and b), the following additional step in which the first person offers the second person the remaining package composed of the stopper and of the support element, by presenting to him the end of said remaining package formed by said support element, orienting said remaining package in such a way that the support element is at a height lower than that of the stopper, such that said article remains contained in the support element during the separation of said support element from the stopper, so as to avoid said article falling to the ground.

This method step applies in particular to an embodiment of the package according to the invention in which the support element forms said first chamber in cooperation with the stopper, and in which said support element is in the form of an elongate hollow body that is open at one end and closed at the other end and is able to contain said article. The first person, referred to as "contaminated", offers the second person, referred to as "clean" or "sterile", the remaining package composed of the stopper and of the support element, by presenting to him the end of said remaining package formed by said support element, orienting said remaining package in such a way that the support element is at a height lower than that of the stopper, such that said article remains contained in the support element during the separation of said support element from the stopper, so as to avoid said article falling to the ground. The second person, or another clean person, is then able, if appropriate with the aid of a tool, to take hold of the article in contact with said support element.

BRIEF DESCRIPTION OF THE DRAWING FIGURES

The invention will be clearly understood from reading the following description of embodiments, with reference to the attached drawings in which.

DETAILED DESCRIPTION OF THE INVENTION

A "dirty" or "contaminated" person is understood as a person working in non-aseptic conditions, who is likely to contaminate the articles he touches with his hands.

Conversely, a "clean" person is understood as a person working in sufficiently aseptic conditions.

With reference to the figures, and as has been mentioned above, the invention relates to a medical assembly comprising a medical article 5 and a package 1 containing said article 5 for the purpose of preserving the sterile nature of the article and with a view to unpacking said article in aseptic or almost aseptic conditions. Said article can be, for example, a solid component, such as a surgical screw, or any other type of article, in particular any other type of implant. In addition, said article can be a liquid or a powder. Said article and, preferably, the various parts of the package are sterilized as detailed below.

Said package comprises a hollow support element 2 inside which said article 5 is free. In other words, said article 5 can move freely inside the support element 2. Said package also comprises a first protective element 3, called a stopper, which can be coupled to the support element 2 of said article 5 by engagement with partial overlap, in such a way that the support element 2 has a grip part 20 that protrudes from said stopper 3. Said grip part 20 corresponds to the free end part of the support element 2 which protrudes from said stopper 3. As is explained in detail below, said support element 2 delimits on its own, or in cooperation with the stopper 3, a first chamber 7 that encloses said article 5.

Said package also comprises a second hollow protective element 4, called a cover. Said cover 4 is able to be coupled to the stopper 3, by engagement with partial overlap, in such a way as to delimit, in cooperation with said stopper 3, a second chamber 8 inside which there extends the grip end 20 of the support element 2. In the state when the cover 4 is coupled to the stopper 3, a part 30 of the stopper 3 protrudes from the cover 4.

Said part 30 of the stopper corresponds to the free end of the stopper 3, opposite the end 31 of said stopper 3 that covers part of the support element 2 and forms a grip area. The end 40 of the cover 4 opposite the stopper 3 also forms a part for gripping the package opposite the end 30 of the stopper.

Thus, each element of the package, namely the support element 2, the stopper 3 and the cover 4, has a grip end 20, 30, 40 in relation to its opposite end coupled to another element of the package. Said elements engage with each other in such a way as to define, by cooperation of two engaged elements, a chamber 7, 8 which is preferably impervious at least to bacteria. Thus, the engaged elements of the package define two chambers 7, 8, of which one 7 is defined between the stopper and the cover, accommodates the article and can be accessed only when opened, the other chamber 8 serving to protect the grip end 20 of the support element 2.

Such a design of the package allows it to be manipulated without risk of contamination of the article contained in the presentation chamber, without having to let go of said article contained in the support element, while at the same time allowing said article to be quickly taken hold of, since the article is free in the support element.

In the example illustrated in the figures, said support element 2 on its own delimits said first chamber 7 enclosing said article 5. For this purpose, said support element 2 is formed by at least two components 20, 21 that can be coupled to/uncoupled from each other, by engagement with partial overlap, in order to form said first chamber enclosing said article 5.

An embodiment can also be provided according to which said support element 2 on its own delimits said first chamber 7 by being formed in one piece. Said support element 2 can thus be in the form of a closed and divisible one-piece hollow body, such as a divisible ampule, containing said article. In this case, the chamber 7 is opened by breaking said ampule.

According to a variant that is not illustrated, said support element delimits, in cooperation with the stopper, said first chamber that encloses said article. In this case, said support element delimits an open cavity intended to be closed by said stopper.

Preferably, the stopper 3 is formed by an elongate hollow body that is open at one end and closed at the other end. In the example illustrated in the figures, the cover 4 is also formed by an elongate hollow body that is open at one end and closed at the other end. The support element 2 is also in the form of an elongate hollow body that is closed at one end and open at the other end, or closed at both ends and formed by at least two components, depending on the embodiment chosen.

The design of the stopper 3 and of the cover 4 in the form of an elongate body, in the manner of a test tube or of a tube closed at least at one end, provides the benefit of, on the one hand, a safe distance between the grip end 40 of the cover 4 and the grip end 30 of the stopper 3, and, on the other hand, a safe distance between the grip end 20 of the support element 2 and the grip end 30 of the stopper 3.

Such a distance between the grip ends 30, 40 of the package makes it possible to limit the risk of contamination in the area of the grip end 20 of the support element 2 that extends in the chamber 8, when said chamber 8 is opened by separation of the cover 4 and the stopper 3.

Said stopper 3, and if appropriate the cover 4, has (have) at least two predefined locations 32 that each permit the positioning of at least one finger of a person in order to allow him to grip said stopper or said cover by gripping between at least two fingers. Preferably, at least two of said predefined locations 32 are diametrically opposite with respect to the axis of the element, i.e. stopper 3 or cover 4, on which they are formed. In the example illustrated in FIGS. 1 to 8 and 8B, each location 32 is formed on a portion of the stopper that is intended to be covered by the cover 4. In this case, said location becomes accessible once the cover has been withdrawn.

Figure 1:
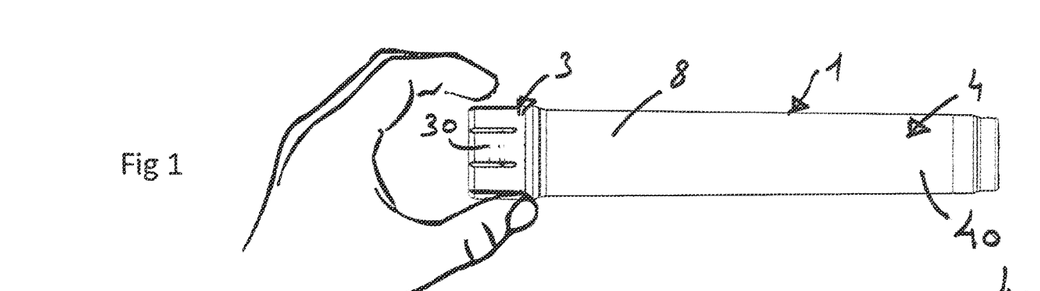
FIG. 1 is a view of a package according to the invention in a first embodiment, inside which a medical component is packed.
Figures 2, 3:
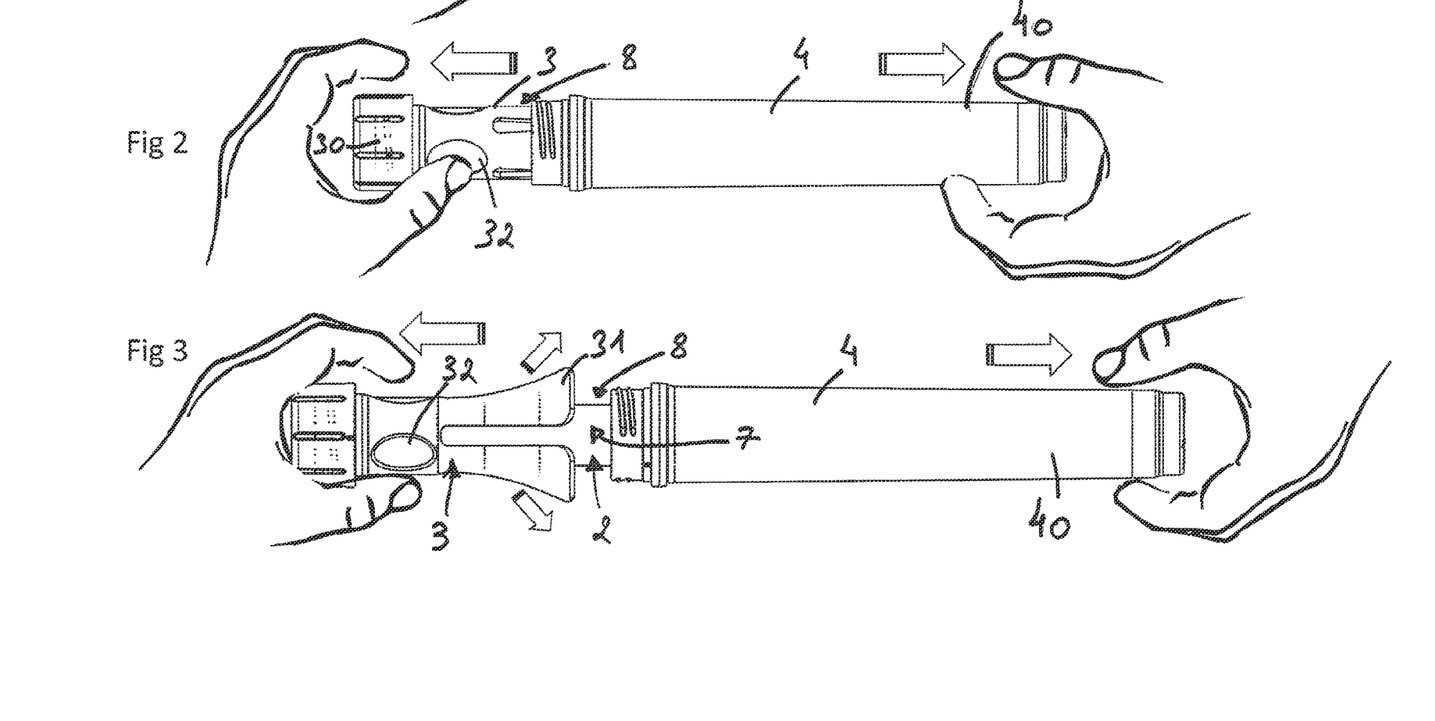
FIGS. 2 to 4 are views of the package from FIG. 1 during a first unpacking step in which the cover is withdrawn by a first person, called the contaminated person, the remaining sub-assembly composed of the stopper and of the support element being held via the stopper by the hand of the contaminated person.
Figure 4:
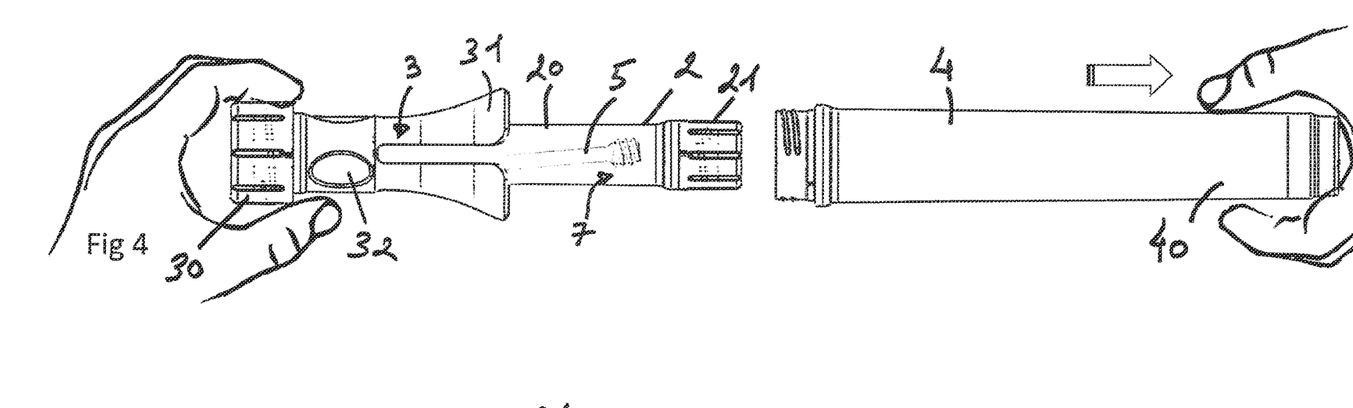
Figure 5:
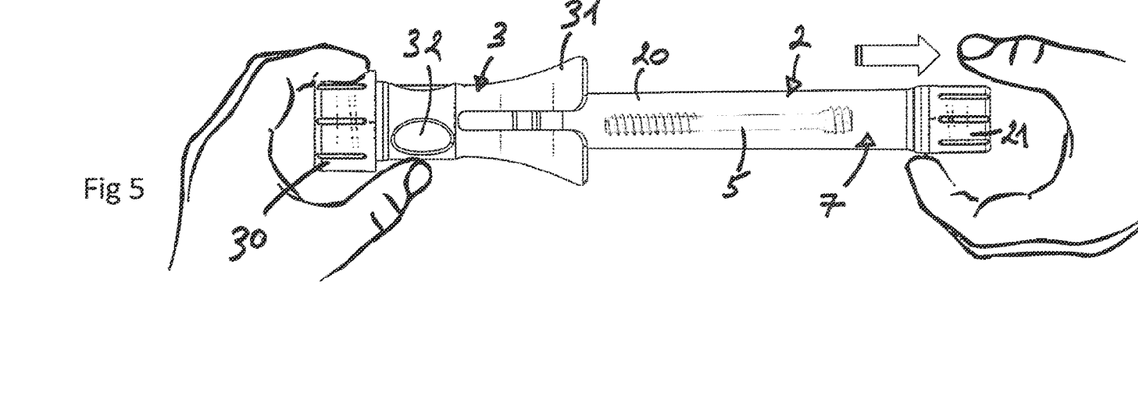
FIGS. 5 and 6 are views of the sub-assembly of the package from FIG. 4 during a second unpacking step in which the stopper is withdrawn, remaining in the hand of the contaminated person, and the support element of the article is held by the hand of a second person called the clean person.
Figure 6:
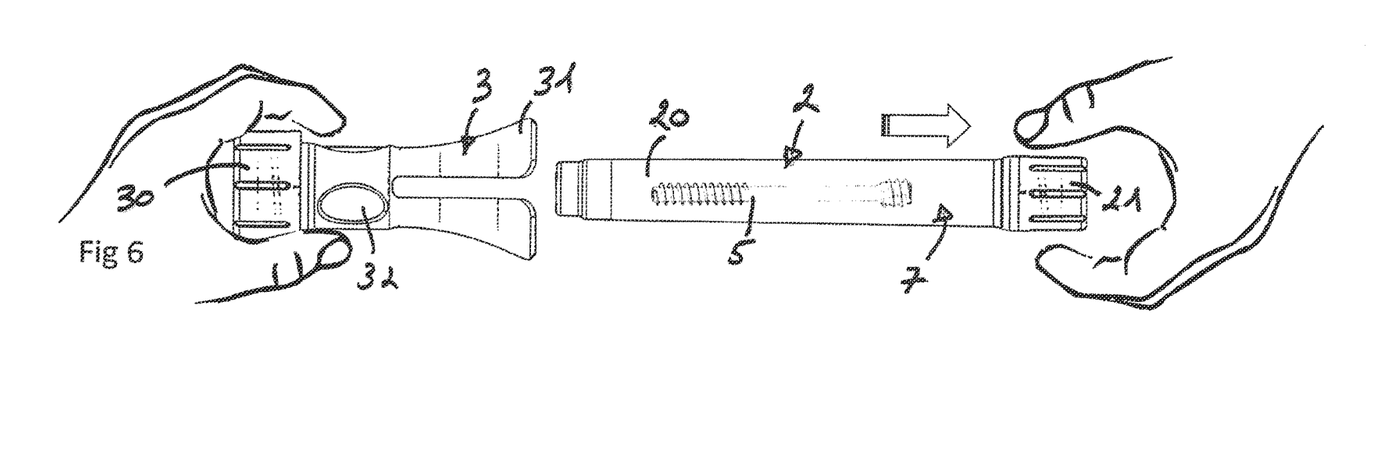
Figure 7:
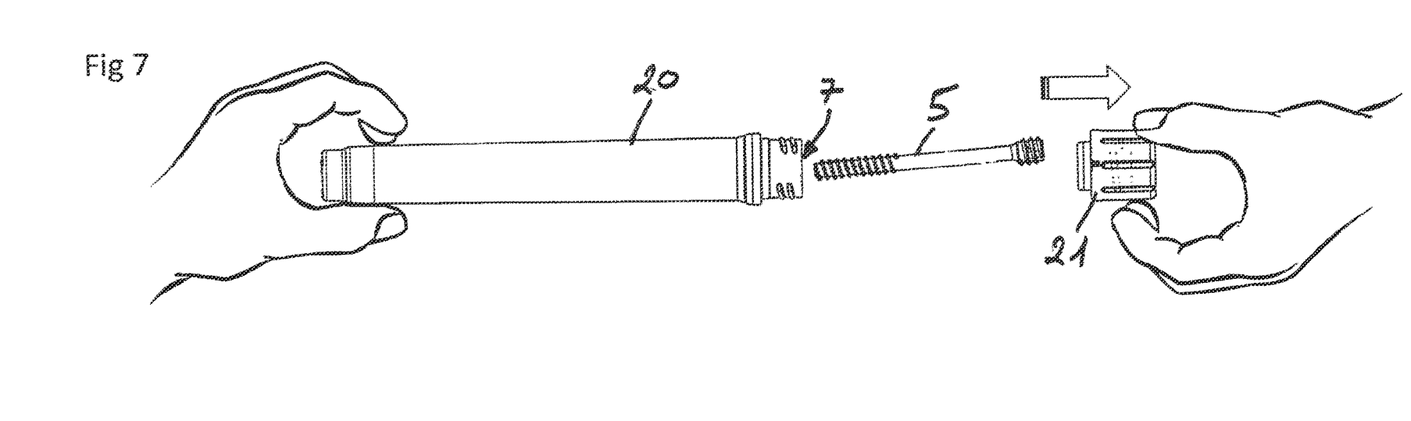
FIG. 7 is a view of the support element from FIG. 5 during a third unpacking step in which the clean person separates the two components forming the support element in order to remove the medical component therefrom.
Figures 8, 8A, 8B:
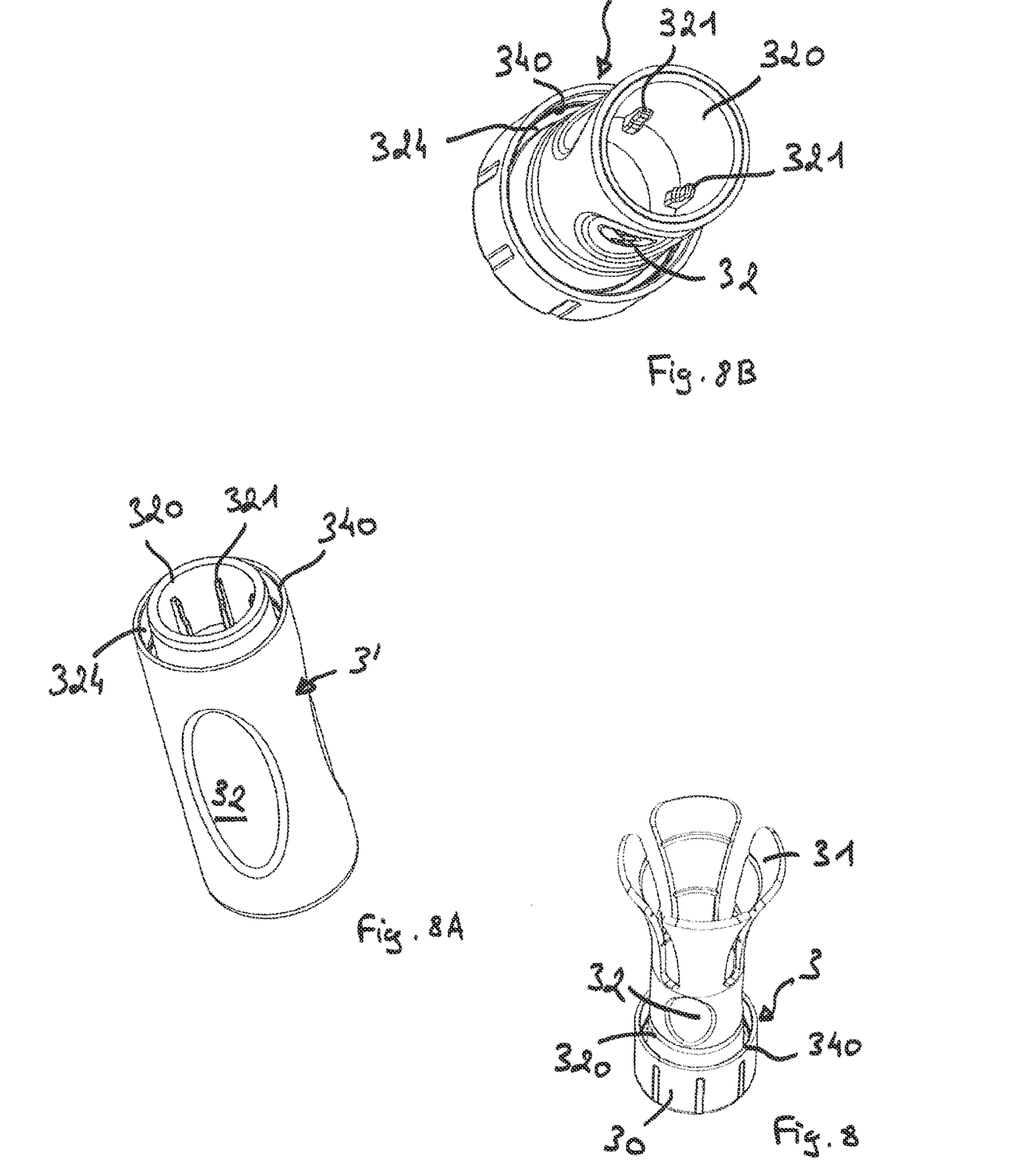
FIG. 8 is a perspective view of the stopper of the package according to the first embodiment of the invention.
FIG. 8A is a perspective view of a variant of the stopper of the package according to the invention, with an area for positioning of the fingers which is called an external area and is formed on that part of the stopper intended to protrude from the cover.
FIG. 8B is a perspective view of another variant of the stopper of the package according to the invention, with an area for positioning of the fingers which is called an internal area and is formed on that part of the stopper intended to extend inside the cover.

According to another embodiment of the stopper 3' illustrated in FIG. 8A, said location 32 is formed on a portion of the stopper 3' that is not intended to be covered by the cover.

Advantageously, the stopper 3; 3' has a sufficient length to allow the person to position his fingers on said stopper, and in particular to grip the stopper with a thumb, without risk of touching the support element 2.

Said support element 2 and protective elements 3, 4 of the package engage each other, with partial overlap, by friction and/or by screwing. The means for coupling the elements to each other are explained in detail below.

In the example illustrated in the figures, the stopper 3 and the cover 4 engage with each other by screwing, as do the parts 20, 21 of which the support element 2 is composed. Preferably, the thread and the tapping formed on the elements which engage with each other are configured in such a way as to allow said elements to be screwed together only once. In particular, provision can be made that the thread and/or the tapping deform during the screwing and unscrewing, such that renewed screwing of the two elements with each other is no longer possible.

Alternatively, the partially overlapping engagement of said elements of the package could be achieved by simple friction, for example by elastic clamping or pressure. Such engagement by simple friction makes it possible to disengage said elements by means of one or each of the persons simply pulling an element of the package in a natural movement. Engagement by clips is also conceivable.

In the example illustrated in FIGS. 1 to 8 and 8B, said stopper 3 also has at least one deformable part 31, preferably at least one deformable wing, allowing said stopper to be partially engaged inside the cover. Said part 31 is configured such that, on the one hand, when said deformable part 31 of the stopper is covered by the cover, said part 31 comes to bear against the internal face of the cover 4 in order to allow the stopper to be coupled to the cover by friction, and, on the other hand, such that said part 31 is able to deform in order to permit the separation of the cover 4 from the stopper 3.

Said stopper 3 is formed by a hollow body open at one end and closed at the other end. The cover 4 is also formed by a hollow body open at one end and closed at the other end. The closed end of the stopper 3 defines a bottom part of the stopper. As is explained in detail below, said stopper 3 comprises means for coupling to the support element 2.

In particular, said stopper 3 comprises a body substantially of revolution about an axis corresponding to the longitudinal axis of said stopper 3. The body of the stopper comprises a peripheral wall 320 called an internal wall, and a peripheral wall 340 called an external wall which surrounds said internal peripheral wall 320.

The external peripheral wall 340 is substantially coaxial to the internal peripheral wall 320.

Said external peripheral wall 340 surrounds said internal peripheral wall 320 with clearance in order to define, between said peripheral walls, an annular space 324 for insertion of that part of the cover 4 intended to be coupled to said stopper 3. Said part of the cover 4 intended to be coupled to said stopper 3 corresponds to the open end of the cover 4.

On the external 340 and/or internal 320 peripheral walls, provision can be made to form screwing means, such as a tapping and/or thread, able to cooperate with complementary screwing means, such as a thread and/or tapping, formed on the peripheral wall of the cover 4.

In particular, the internal face of the peripheral wall 340 called the external wall and/or the external face of the peripheral wall 320 called the internal wall can have a tapping and/or a thread in order to cooperate with a complementary thread and/or tapping formed on the external peripheral face and/or the internal peripheral face of the body of the cover 4.

In the example illustrated in the figures, the internal face of the external peripheral wall 340 has a tapping able to cooperate with a thread formed on the external face of the peripheral wall of the cover 4.

Provision can also be made that the distance between the external 340 and internal 320 peripheral walls of the stopper is configured such that the engagement of the cover 4 with the stopper 3 causes the peripheral wall of the cover 4 to be pinched between the external 340 and internal 320 peripheral walls of the stopper.

In the example illustrated in the figures, the stopper 3 and the support element 2 engage with each other by force, that is to say by pressing an end part of the support element 2 into a corresponding hollow part of the stopper 3.

In other words, the internal face of the internal peripheral wall 320 of the stopper 3 has retaining means 321 for retaining the part of the support element engaged by force inside the space delimited by the internal peripheral wall 320 of the stopper 3.

Advantageously, said retaining means 321 comprise lugs which are intended to be in bearing contact with the support element 2 in the state when said support element 2 is driven into the stopper 3. A good retention of the support element 2 with the stopper 3 is thus obtained before their separation with a view to opening said first chamber 7. In particular, each lug has a ramp-forming part configured such that the support element 2, which is engaged in the internal peripheral wall 320, pushes the lugs radially outward and thus deforms the corresponding internal peripheral wall 320 toward the external peripheral wall 340.

More precisely, as is illustrated more particularly in FIGS. 8A and 8B, the lugs 321 are distributed on the internal peripheral face of the stopper, about the axis of said stopper 3, preferably being spaced apart at angles from one another.

The presence of said lugs inside the internal peripheral wall 320 of the stopper makes it possible to retain the support element 2 engaged by force in the stopper 3, while also ensuring that, on such engagement of the support element 2 in the internal peripheral wall of the stopper, the internal peripheral wall 320 of the stopper is brought closer to the external peripheral wall 340 of said stopper, this being caused by the support element 2 bearing on the lugs 321.

The closing together of the internal 320 and external 340 peripheral walls by elastic deformation reinforces the leaktightness of the join in the area of engagement between the cover 4 and the stopper 3. This is because the peripheral walls 320, 340 can thus pinch the peripheral wall of that part of the stopper 3 engaged in the space formed between said internal 320 and external 340 peripheral walls of the stopper.

Thus, said retaining means 321 formed inside the internal peripheral wall 320 of the stopper 3 make it possible to improve not only the hold of the support element 2 with respect to the stopper 3, but also the leaktightness between the stopper 3 and the cover 4, of which the peripheral wall is pinched between said internal 320 and external 340 peripheral walls of the stopper 3.

In the example illustrated in the figures, the hold between the cover 4 and the stopper 3 is ensured by the complementary screwing means, of the thread and tapping kind, formed on the cover 4 and the stopper 3, and the leaktightness between the cover 4 and the stopper 3 is obtained by pinching the peripheral wall of the cover 4 between said peripheral walls 320 and 340 of the stopper 3, resulting from the engagement of the support element 2 in the stopper 3 which elastically deforms the peripheral wall 320 toward the peripheral wall 340 of the stopper 3. The retention of the support element in the stopper 3 is ensured by the lugs 321 which enclose the support element 2.

In addition, the lugs 321 form spacers between the peripheral wall 320 and the support element 2, which spacers allow a radial distance to be maintained between the support element 2 and the peripheral wall 320. In addition, the spacing between the lugs 321 makes it possible to define a space for fluid communication between the inside of the peripheral wall 320 and the inside of the cover 4.

A communication passage of this kind between the inside of the cover 4 and the inside of the peripheral wall 320 ensures that a sterilization gas injected into the cover 4, for example via a membrane permeable to gas and preferably impermeable to bacteria, is able to spread inside the volume delimited by the peripheral wall 320, in order to sterilize the two chambers 7 and 8 of the package, especially when the support element 2 is an open element, or when that end of the support element 2 engaged in the peripheral wall 320 has a membrane permeable to gas and preferably impermeable to bacteria.

Provision can be made that the retaining means 321 for retaining the support element 2 with respect to the stopper 3 also comprise screwing means, for example of the tapping kind, which are able to cooperate with complementary screwing means, for example of the thread kind, which are formed on the external face of the peripheral wall of the support element 2.

The combination of screwing means and of lugs thus makes it possible to combine a retention of the support element 2 with respect to the stopper 3 by screwing and also by friction, while maintaining the aforementioned advantages of the join between the stopper 3 and the cover 4.

In addition, in the example illustrated in the figures, the internal peripheral wall 320 protrudes from the external peripheral wall 340 at the end opposite the bottom of the stopper 3.

According to the stopper variants that are illustrated in FIGS. 8A and 8B, the stoppers 3'; 3" also each have a hollow part which is provided with lugs and into which an end part of the corresponding support element is intended to be driven.

The support element 2 and/or the stopper 3 and/or the cover 4 have a part, preferably formed by a membrane, that is impermeable to bacteria but permeable to gases in order to permit gas sterilization of said first chamber 7 and/or of said second chamber 8.

With the package described above, it is possible to carry out a method of unpacking that comprises the following steps. This method is described with reference to FIGS. 1 to 8 in which the support element is composed of two components which can be coupled/uncoupled in order to delimit a closed cavity that encloses said article. As is illustrated in FIGS. 1 to 4, a first person, presumed to be in a contaminated area, separates the cover 4 from the stopper 3 in such a way as to uncover the support element 2, which remains away from the hands of the person who is presumed to be contaminated, since the hand of said person holds the remaining package by the stopper 3, that is to say at a distance away from the support element. The contaminated person can then offer to a second person, presumed to be in a clean area, the remaining package via the support element 2. Said clean person can then pull the support element 2 in order to cause the separation of said support element 2 from the stopper 3 held by the first person, who is presumed to be contaminated. Said "clean" person is, for example, the surgeon in the operating theater.

If appropriate, the support element 2 which encloses the article 5 can be kept in a stand-by area pending the use of said article 5. Then said second person, or another person presumed to be clean, can open the first chamber 7 defined by said support element 2 by separating, in this case by unscrewing, the two components 20, 21 which form said support element, in order to take hold of said medical component.

In the case not illustrated in the figures, where the support element directly forms the first chamber accommodating said article in cooperation with the stopper, the method described above is adapted such that the contaminated person offers to the second person, presumed to be in a clean area, the remaining package via the support element 2, by orienting said remaining package in such a way that the support element 2 is at a height lower than that of the stopper 3, such that said article 5 remains contained in the support element 2 during the separation of said support element 2 from the stopper 3, so as to avoid said article 5 falling to the ground.

Thus, the medical component has not been touched or let go of during its unpacking. In addition, the chamber containing the medical component is opened only in a clean area.

By virtue of the cover which delimits a chamber protecting the grip part 20 of the support element 2, the clean person touches a clean part of the package. This is because the dirty parts of the package, namely the stopper 3 and the cover 4, have remained in the hands of the dirty person. It is thus ensured that the hand of the person taking hold of the support element remains clean.

Of course, in each of the embodiments, provision can be made that the separation of the cover and the stopper is carried out by two different persons in a contaminated area instead of by only one person, one of them holding an end of the stopper and the other holding an end of the cover.

Preferably, the chambers 7 and 8 are impermeable at least to bacteria. Provision can be made that they are also impermeable to any fluid. Alternatively, provision can be made that one or other of them, preferably at least the chamber 7 for presentation of the article, is permeable only to gases in order to permit gas sterilization of the one or more chambers.

Thus, according to a particular embodiment of the invention, provision can be made that at least part of the wall of the stopper 3 delimiting part of the chamber 7 for presentation of the article 5 is made of material permeable to gas but impermeable to bacteria, in order to permit gas sterilization of the chamber for presentation of the article, for example a medical component, for example with ethylene oxide or by steam. Such a design of the package allows the one or more chambers to be sterilized other than by radiation.

Provision can thus be made that the stopper, at its end opposite the one partially covering the support element, is closed by a membrane designed for gas sterilization.

The present invention is not in any way limited to the embodiments that have been described and illustrated, and instead a person skilled in the art will be able to apply any variant thereof that he sees fit.

The invention claimed is:

1. A medical assembly comprising a medical article and a package containing said article,
    said package comprising a hollow support element in which said article is free, wherein said package comprises:
    a stopper configured to be coupled to the hollow support element of said article in such a way that the hollow support element has a grip part that protrudes from said stopper, said grip part of the hollow support element being adapted to be held by a hand of a person;
    said hollow support element delimiting on its own, or in cooperation with the stopper, a first chamber that encloses said article,
    a hollow protective cover configured to be coupled to the stopper in such a way as to delimit, in cooperation with, said stopper, a second chamber inside which there extends the grip part of the hollow support element, said hollow protective cover being also separable from the stopper,
    and in that, in the state when the hollow protective cover is coupled to the stopper, a part of the stopper protrudes from the hollow protective cover, and is configured to form a grip end of the stopper that is adapted, in the state wherein the hollow protective cover is separated from the stopper, to be held by a hand of a person;
    wherein a part of the hollow support element is engaged by force inside the stopper, and, when the hollow protective cover is separated from the stopper, the hollow support element remains coupled to the stopper while said hollow support element is also separable from said stopper when a person holds the grip part of said hollow support element and pulls said hollow support element so as to separate it from said stopper;

wherein said stopper comprises an internal peripheral wall, and an external wall peripheral wall which surrounds said internal peripheral wall with clearance in order to define, between said peripheral internal and external walls, an annular space for engagement of that part of the hollow protective cover intended to be coupled to said stopper, the internal peripheral wall defining a space for engagement of that part of the hollow support element intended to be coupled to said stopper, wherein an internal face of the internal peripheral wall of the stopper is provided with retaining means for retaining that part of the hollow support element engaged inside the space delimited by said internal peripheral wall of the stopper, and wherein said retaining means comprise lugs which are intended to be in bearing contact with the hollow support element in the state when said hollow support element is engaged in the stopper, and wherein the lugs are distributed on the internal peripheral face of the stopper, about the axis of said stopper, by being spaced apart at angles from one another.

2. The medical assembly as claimed in claim 1, wherein each lug comprises a ramp-forming part, directed toward the axis of the stopper starting from a bottom point of the ramp situated at the open end of the stopper to a top point of said ramp situated at the closed end of said stopper, in such a way that, when the hollow support element is engaged inside the space defined by the internal peripheral wall of the stopper, said hollow support element, by bearing on said ramp, pushes said lug radially and deforms the corresponding internal peripheral wall toward the external peripheral wall.

3. The medical assembly as claimed in claim 2, wherein the lugs form spacers for maintaining a radial distance between the hollow support element and the internal peripheral wall of the stopper, the spacing between the lugs defining a space for fluid communication between the inside of the internal peripheral wall of the stopper and the inside of the hollow protective cover.

4. The medical assembly as claimed in claim 1, wherein the lugs form spacers for maintaining a radial distance between the hollow support element and the internal peripheral wall of the stopper, the spacing between the lugs defining a space for fluid communication between the inside of the internal peripheral wall of the stopper and the inside of the hollow protective cover.

5. The medical assembly as claimed in claim 1, wherein, when said hollow support element delimits on its own said first chamber enclosing said article, said hollow support element is formed by at least two components that can be coupled to/uncoupled from each other in order to form said first chamber enclosing said article.

6. The medical assembly as claimed in claim 5, wherein said at least two components configured to be coupled to/uncoupled from each other, by engagement with partial overlap, in order to form said first chamber enclosing said article.

7. The medical assembly as claimed in claim 1, wherein, when said hollow support element delimits, in cooperation with the stopper, said first chamber enclosing said article, said hollow support element delimits an open cavity intended to be closed by said stopper.

8. The medical assembly as claimed in claim 1, wherein said stopper has predefined locations permitting the positioning of at least two fingers of a person in order to allow him to grip said stopper in the area of said predefined locations.

9. The medical assembly as claimed in claim 1, wherein at least one of the hollow support element, the stopper, and the hollow protective cover has a part that is impermeable to bacteria but permeable to gases in order to permit gas sterilization of at least one of said first chamber and said second chamber.

10. The medical assembly as claimed in claim 9, wherein said part is formed by a membrane.

11. The medical assembly as claimed in claim 1, wherein the medical assembly is a sterilized one.

12. The medical assembly as claimed in claim 1, wherein the stopper can be coupled to the hollow support element of said article by engagement with partial overlap.

13. The medical assembly as claimed in claim 1, wherein the hollow protective cover is able to be coupled to the stopper by engagement with partial overlap.

14. The medical assembly as claimed in claim 1, wherein said hollow protective cover has predefined locations permitting the positioning of at least two fingers of a person in order to allow them to grip said hollow protective cover, in the area of said predefined locations.

15. A medical assembly comprising a medical article and a package containing said article,
    said package comprising a hollow support element in which said article is free, wherein said package comprises:
    a stopper configured to be coupled to the hollow support element of said article in such a way that the hollow support element has a grip part that protrudes from said stopper, said grip part of the hollow support element being adapted to be held by a hand of a person;
    said hollow support element delimiting on its own, or in cooperation with the stopper, a first chamber that encloses said article,
    a hollow protective cover configured to be coupled to the stopper in such a way as to delimit, in cooperation with, said stopper, a second chamber inside which there extends the grip part of the hollow support element, said hollow protective cover being also separable from the stopper,
    and in that, in the state when the hollow protective cover is coupled to the stopper, a part of the stopper protrudes from the hollow protective cover, and is configured to form a grip end of the stopper that is adapted, in the state wherein the hollow protective cover is separated from the stopper, to be held by a hand of a person;
    wherein a part of the hollow support element is engaged by force inside the stopper, and, when the hollow protective cover is separated from the stopper, the hollow support element remains coupled to the stopper while said hollow support element is also separable from said stopper when a person holds the grip part of said hollow support element and pulls said hollow support element so as to separate it from said stopper;
    wherein said stopper comprises an internal peripheral wall, and an external wall peripheral wall which surrounds said internal peripheral wall with clearance in order to define, between said peripheral internal and external walls, an annular space for engagement of that part of the hollow protective cover intended to be coupled to said stopper, the internal peripheral wall defining a space for engagement of that part of the hollow support element intended to be coupled to said stopper, and
    wherein at least one of said external and internal peripheral walls of the stopper comprise screwing means for cooperating with complementary screwing means formed on the hollow protective cover.

16. The medical assembly as claimed in claim 15, wherein the internal face of the external peripheral wall of the stopper has a tapping that is able to cooperate with a thread formed on the external face of a peripheral wall of the hollow protective cover.

17. A method of unpacking a medical article contained in a package of a medical assembly as claimed in claim 1, wherein said method comprises the following steps:
   separation of the hollow protective cover from the stopper by a first person in order to uncover the hollow support element,
   gripping of the hollow support element by a second person,
   separation of said hollow support element from the stopper held by the first person.

18. The method of unpacking as claimed in claim 17, wherein said method comprises the following additional step of opening the first chamber defined by said hollow support element in order to remove said article therefrom.

19. The method of unpacking as claimed in claim 18, wherein said method comprises the following additional step before the opening step of keeping said hallow support element, which encloses the article, in a stand-by area pending the use of said article.

20. The method of unpacking as claimed in claim 17, wherein said method comprises, between said separation step and said gripping step, the following additional step in which the first person offers the second person the remaining package composed of the stopper and of the hollow support element, by presenting to him the end of said remaining package formed by said hollow support element, orienting said remaining package in such a way that the hollow support element is at a height lower than that of the stopper, such that said article remains contained in the hollow support element during the separation of said hollow support element from the stopper, so as to avoid said article falling to the ground.

* * * * *